United States Patent [19]

Melrose et al.

[11] Patent Number: 4,678,914

[45] Date of Patent: Jul. 7, 1987

[54] DIGITAL IR GAS ANALYZER

[75] Inventors: Richard C. Melrose; Lionel D. McIntosh, both of Huntsville, Ala.

[73] Assignee: Environmental Tectonics Corporation, Southhampton, Pa.

[21] Appl. No.: 605,702

[22] Filed: Apr. 30, 1984

[51] Int. Cl.⁴ .................................. G01J 1/00
[52] U.S. Cl. ............................ 250/343; 250/352
[58] Field of Search ................ 250/343, 351, 352

[56] References Cited

U.S. PATENT DOCUMENTS

| | | | |
|---|---|---|---|
| 3,725,701 | 4/1973 | Link | 250/43.5 |
| 3,780,293 | 12/1973 | Flint | 250/351 |
| 3,790,797 | 2/1974 | Sternberg et al. | 250/345 |
| 3,790,798 | 2/1974 | Sternberg et al. | 250/345 |
| 3,887,473 | 6/1975 | Sternberg et al. | 250/345 |
| 3,979,589 | 9/1976 | Sternberg et al. | 250/252 |
| 4,013,260 | 3/1977 | McClatchie et al. | 250/343 |
| 4,027,972 | 6/1977 | Davies | 356/51 |
| 4,083,367 | 4/1978 | Portner et al. | 128/2.07 |
| 4,103,174 | 7/1978 | McClatchie et al. | 250/493 |
| 4,163,899 | 8/1979 | Burough | 250/343 |
| 4,177,381 | 12/1979 | McClatchie et al. | 250/343 |
| 4,200,791 | 4/1979 | Burough | 250/343 |
| 4,233,513 | 11/1980 | Elder et al. | 250/343 |
| 4,241,309 | 12/1980 | Elder | 328/115 |
| 4,346,296 | 8/1982 | Passaro et al. | 250/343 |
| 4,398,091 | 8/1983 | Passaro | 250/343 |

Primary Examiner—Janice A. Howell
Attorney, Agent, or Firm—Seidel, Gonda, Goldhammer & Abbott

[57] ABSTRACT

A digital IR gas analyzer comprises a sample cell having a conical shaped interior wall and a filter wheel provided with HC, CO and CO2 interference filters. The filter wheel and IR detector are temperature stabilized. The HC, CO and CO2 gas samples are normalized to a precision reference voltage. The normalized samples are digitized and processed, i.e., for linearization, cross-talk correction and zero drift temperature compensation, by a digital processor. The processed samples are then converted to analog to drive HC, CO and CO2 meters. HC, CO and CO2 gas channels are zeroed simultaneously and calibrated automatically in response to control panel switches.

6 Claims, 23 Drawing Figures

```
( FRAME A )
     |
[ FILTER
  RESPONSE ]
     |
[ CROSS TALK
  DISABLE ON
  AUTO ZERO ]
```

FIG. 15F

```
( FRAME B )
     |
[ RANGE
  SELECT ]
     |
[ IR SOURCE
  CONTROL ]
     |
[ AUTO ZERO
  HC, CO COARSE
  COMPUTE B FOR
  HC, CO, CO2 ]
     |
[ SPAN DRIFT
  CO ]
```

FIG. 15G

```
( FRAME C )
     |
[ UPDATE
  RAM ON
  CALIBRATION ]
     |
[ HEATER
  PREHEAT
  INITIALIZE
  TRACK ]
     |
[ SPAN DRIFT
  HC ]
```

DIGITAL IR GAS ANALYZER

BACKGROUND OF THE INVENTION

The present invention is directed to an IR gas analyzer for measuring the concentrations or amounts of constituent gases in a sample gas mixture. The sample gas mixture may be taken from the exhaust of an automobile engine wherein the constituent gases are HC, CO and CO2.

DETAILED DESCRIPTION OF INVENTION

Figure 1A:
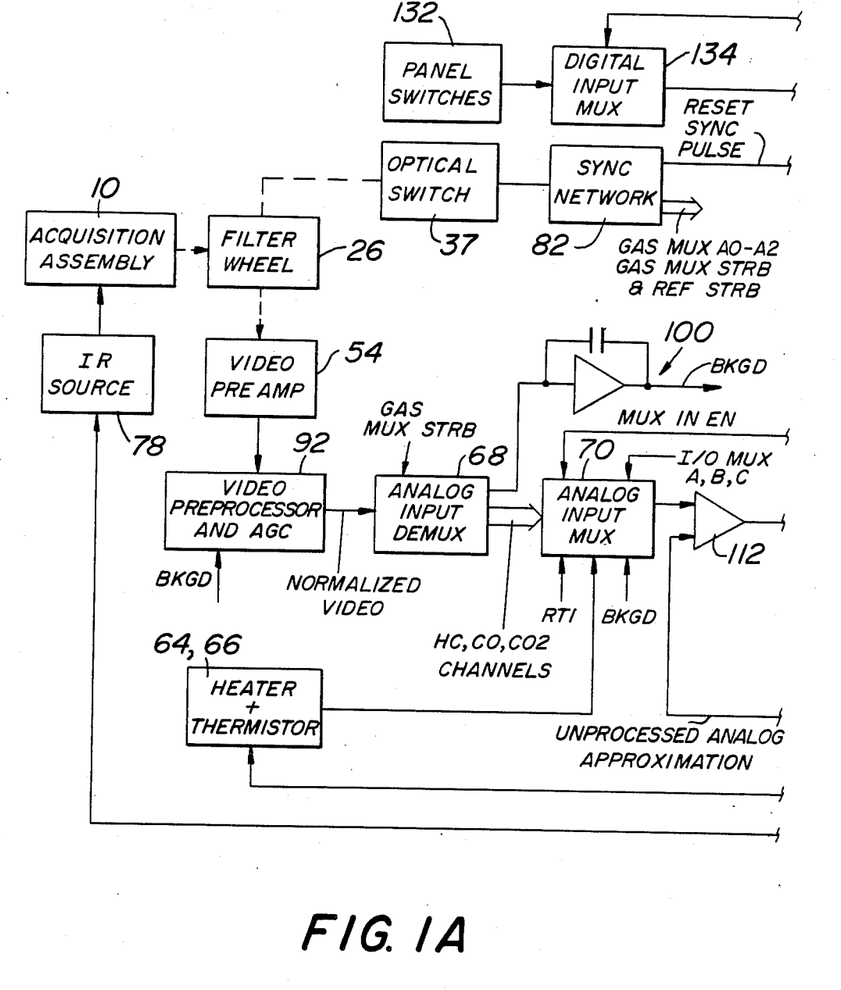
FIGS. 1A and 1B comprise a functional block diagram of the gas analyzer of the present invention.
Figure 1B:
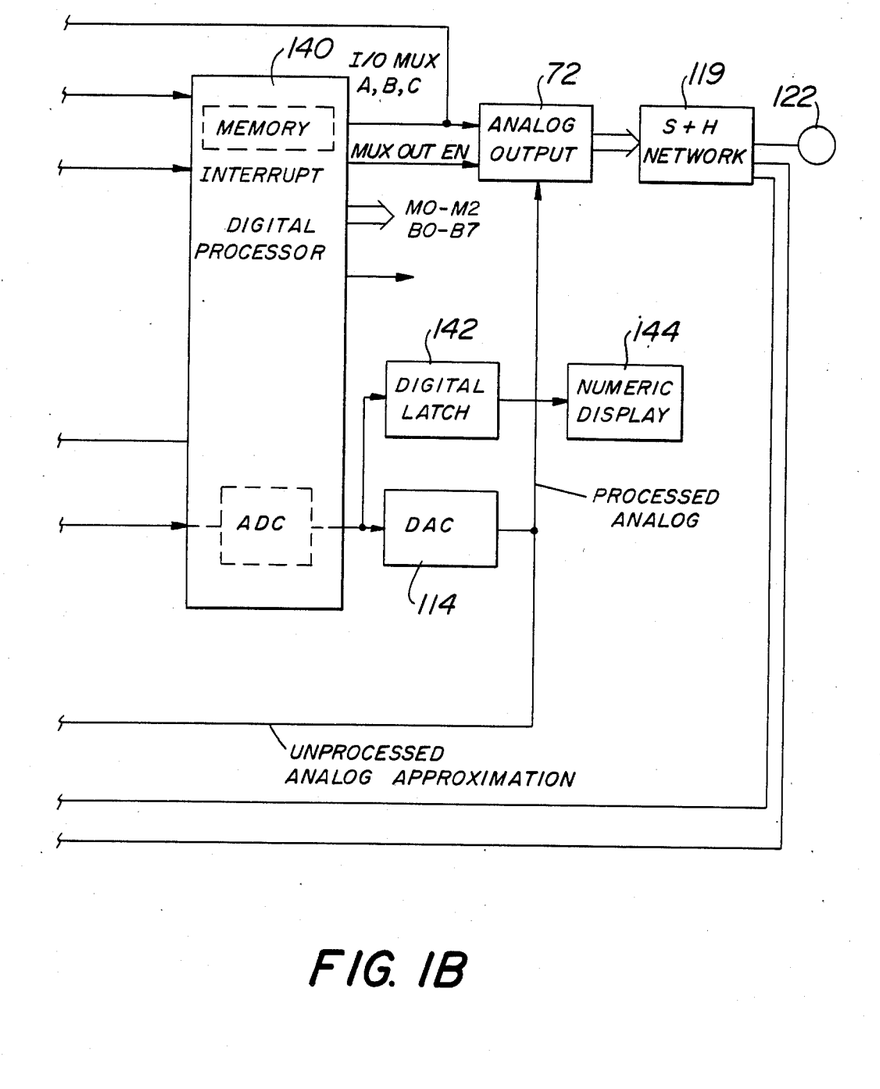

Referring to the drawings wherein like numerals indicate like elements, there is shown in FIG. 1 a functional block diagram of the digital IR gas analyzer of the present invention. The analyzer includes a constant speed, motor driven filter wheel 26 which derives IR optical samples of constituent gases such as HC, CO and CO2. The optical samples are detected and then normalized to a precision 5 volt reference by a video preamplifier 54 and video preprocessor 92.

The normalized video samples appear in time multiplexed format at the preprocessor output and are demultiplexed into HC, CO and CO2 gas channel samples by an analog input demultiplexor 68. The gas channel outputs of demultiplexor 68 are multiplexed by analog input multiplexor 70 and converted to digital by a comparator 112 and digital to analog converter (DAC) 114 in combination with the digital processor 140.

The digitized samples are then processed, i.e., scaled, linearized and corrected for channel cross-talk and zero drift with temperature, by the digital processor. The processed samples are then converted by DAC 114 to analog and transmitted by an analog output demultiplexor 72 to a sample and hold network 119. Sample and hold gates in network 119 drive an analog HC meter, an analog CO meter and an analog CO2 meter, the meters being designated generally as 122 in FIG. 1.

The DAC 114 serves a dual purpose. During digitization of a gas channel sample input, digital approximations of the sample are successively transmitted to the DAC by the digital processor. The DAC converts each approximation to analog and transmits the same to comparator 112 for comparison to the sample input until a match is obtained. Each digitized gas channel sample is then processed by the digital processor and transmitted by DAC 114 and analog output multiplexor 72 to the sample and hold network 119.

Timing for the digital processor is provided by a sychronization (sync) network 82 in response to an optical switch 37 which is actuated by a filter wheel 26. The synchronization network outputs are sync pulses which identify the gas channel samples based on filter wheel position.

The analog meters 122 are zeroed and calibrated automatically by the digital processor in response to outputs generated by panel switches 132 via digital input multiplexor 134.

The processed digitized gas channel samples at the DAC 114 input are latched by a digital latch 142 which drives a digital numeric display 144. Display 144 provides numeric indications of the HC, CO and CO2 sample values.

Figure 2:
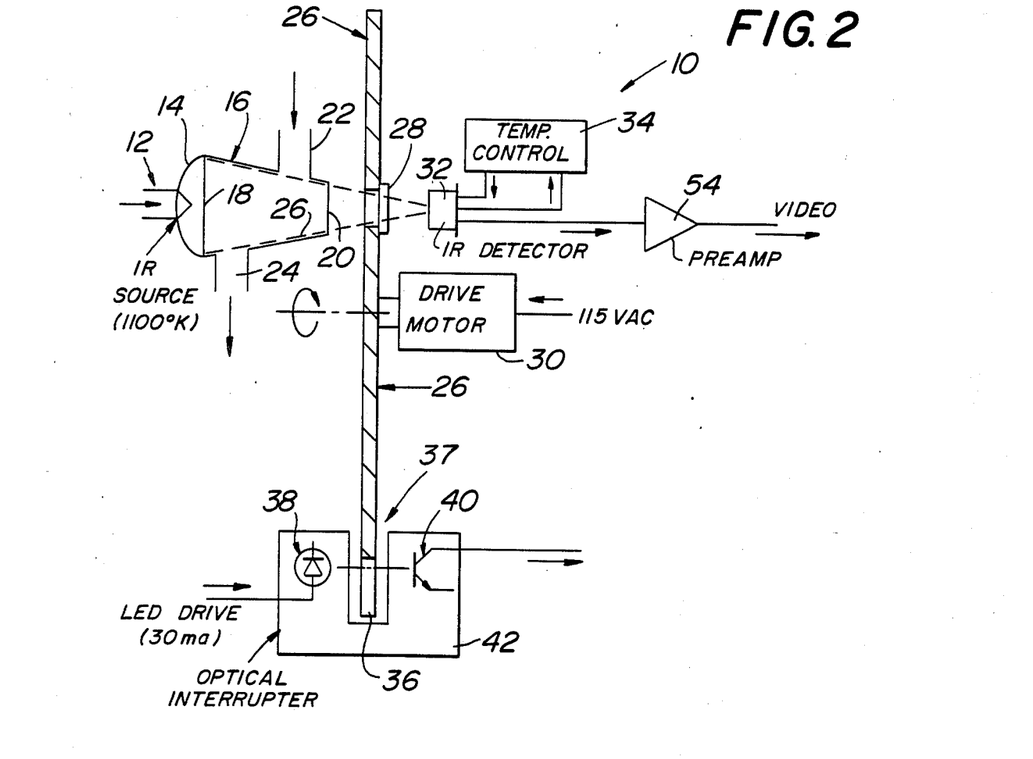
FIG. 2 is a diagram of the acquisition assembly.

The acquisition assembly 10 of the digital IR gas analyzer of the present invention is shown in FIG. 2. The acquisition assembly includes an IR source 12, parabolic reflector 14 and a sample cell 16. IR radiation is generated by source 12 and focused by parabolic reflector 14 so as to pass through a mica window 18 at the source side of the sample cell. Preferably, IR source 12 is a 0.1 inch diameter chromel-C helix positioned near the focus of the parabolic reflector 14. The parabolic reflector is made of aluminum and preferably has a diameter of 1.5 inches. The aluminum is coated with a 2-5 micron SiO layer which prevents vaporization of the aluminum surface into Al2O3 by the IR radiation. Vaporization of the aluminum would fog the mica window 18.

The IR source is operated at 1100° K. and produces approximately 200 milliwatts of radiated power in the 3-5 micron band. Focused IR radiation traverses the sample cell and passes through a sapphire outlet window 20. A sapphire window is preferred because it is not subject to warping at elevated operating temperatures. Sample gas such as automobile engine emission is introduced to the sample cell inlet port 22. The sample gas flows through the cell and exits the cell at outlet port 24. Ports 22 and 24 are spaced apart along the longitudinal axis of the sample cell. IR radiation is absorbed in varying amounts by the HC, CO and CO2 constituents of the sample gas. The interior wall 26 of the sample cell is conical shaped, converging in the direction of window 20. IR radiation passes through window 20 and impinges on filter wheel 26 at a predetermined radius along which a series of interference filters, designated generally as 28 in FIG. 2, are located.

Figure 3:
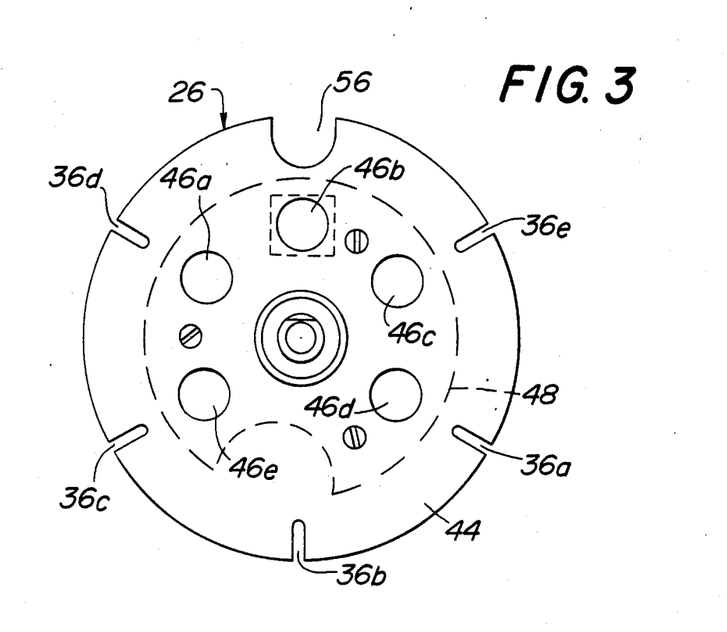
FIG. 3 is a front elevation of the filter wheel.

The filter wheel 26 is driven by a sychronous motor 30. Motor 30 drives the filter wheel at a constant speed, for example 3600 revolutions per minute. An IR detector 32 is mounted behind the filter wheel, at an elevation corresponding to the position of an interference filter 28 when the filter is aligned with outlet window 20. The IR detector is temperature stabilized by a temperature control 34. A series of spaced radial slots, designated generally as 36 in FIG. 3, is formed at the periphery of the filter wheel. The wheel is positioned so that the slots 36 periodically actuate optical switch 37 (FIG. 2) by establishing an optical path between a LED source 38 and an optical sensor 40 mounted in facing relation across a gap in a mounting block 42.

The filter wheel 26 comprises a two inch diameter black Valox circular plate 44 provided with radial spaced slots 36a, b, c, d, and e at its periphery. See FIG. 3. Each slot is approximately 0.040 inches wide. A series of circular holes 46a, b, c, d, e are formed in the wheel at a common radius of 0.7 inches. An enlarged slot 56 is formed in the periphery of the plate for the purpose of generating a reset pulse. Slot 56 is approximately seven times as wide as each of the slots 36a, b, c, d and e.

Figure 4:
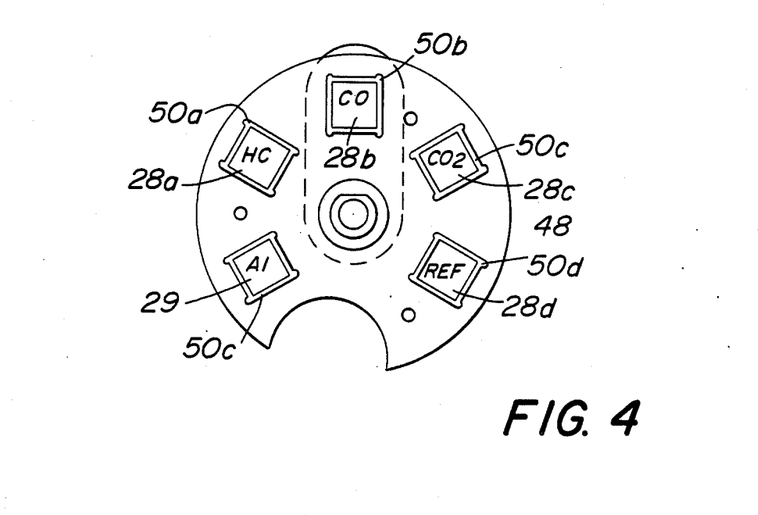
FIG. 4 is a rear elevation of the filter wheel retainer plate.

A retainer plate 28 is mounted on the back of plate 44. See FIG. 4. The retainer plate is provided with five holders 50a, b, c, d and e. Interference filters 28a, b, c, and d are inserted in holders 50a, b, c, d respectively. An aluminum slug 29 is inserted in holder 50e for the purpose of measuring background IR.

Filter 28a has a transmission bandwidth centered at 3.40 microns which is the IR absorption peak of HC. Filter 28b has a transmission bandwidth centered at 4.60 microns which is the IR absorption peak of CO. Filter 28c has a transmission bandwidth centered at 4.425 microns which is the IR absorption peak of the C13 isotope found in CO2. Filter 28d is a reference filter which has a transmission bandwidth centered at 3.90 microns. The aluminum slug transmits no IR and, instead, reflects IR back to the sample cell. For each of the interference filters, the half-bandwidth, i.e., the wave length difference between half power points on the filter response curve, is approximately 2-3 percent of the center wavelength of the band. The transmission bands of the interference filters are non-overlapping.

As previously noted, the CO2 filter is centered at the absorption peak of the C13 isotope.

Since the ratio of the C12 and C13 isotopes is always constant in CO2, detection of the C13 absorption peak enables measurement of the C12 isotope as well.

Measurement of an HC, CO or CO2 constituent in an automobile emission is accomplished in the present invention by transmitting broad band IR through the sample cell and by measuring the amount of IR energy remaining within the absorption band of the constituent. The amount of IR energy remaining within the absorption band of a constituent is detected by the IR detector 32. The output of the IR detector is fed to preamplifier 54 (FIG. 1). The video output of the preamplifier is normalized by preprocessor 92. The normalized video is shown in curve (a) of FIG. 5 as a sequence of constituent samples. The amplitude of each constituent sample is proportional to the energy received by the IR detector in the particular transmission bandwidth of an interference filter.

Figure 5A:
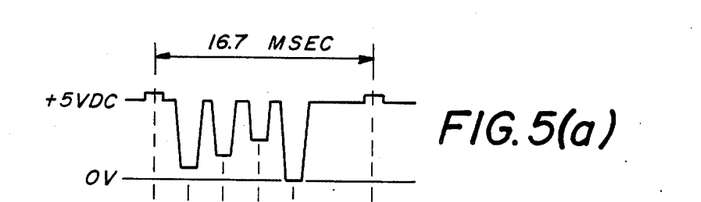
FIG. 5 shows the normalized video and sync pulse wave forms.
Figure 5B:
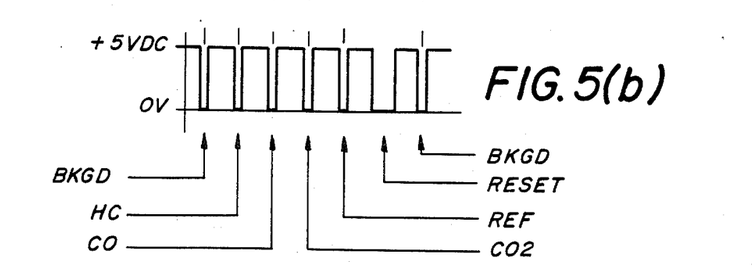

Curve (b) of FIG. 5 shows the sychronization (sync) pulses which are developed by the optical sensor 40 as the filter wheel rotates. As described in fuller detail hereafter, the sync pulses are used for digital processor timing and to identify each video pulse produced by preamplifier 54. The first synch pulse is the background (BKGD) sync pulse which occurs when slot 36e crosses the path between LED source 38 and optical sensor 40. At this time, hole 46e and slug 29 (FIG. 3) are in alignment with sample cell window 20. Accordingly, no IR reaches IR detector 32 from the sample cell. The IR detector detects only background IR and generates a background (BKGD) video pulse proportional to the background IR. As the filter wheel rotates, slot 36a aligns with LED source 38 and optical sensor 40, and the sensor generates a second sync pulse which is the HC sync pulse. At this time, the HC filter 28a aligns with sample cell window 20. The IR detector 32 receives IR from the sample cell in the transmission bandwidth of the HC filter and develops a HC video pulse which is proportional to the received radiation. Slot 36b then moves into alignment with source 38 and sensor 40, and the sensor generates a third sync pulse which is the CO sync pulse. At this time, the CO filter 28b aligns with sample cell window 20. The IR detector receives IR from the sample cell in the transmission bandwidth of the CO filter, and the detector develops a CO video pulse which is proportional to the received radiation. Slot 36c then moves into alignment with source 38 and sensor 40, and the sensor develops a fourth sync pulse which is the CO2 sync pulse. At this time, CO2 filter 50c moves into alignment with sample cell window 20. The IR detector receives IR from the sample cell in the transmission bandwidth of the CO2 filter, and the detector develops a CO2 video pulse proportional to the received radiation. Slot 36d then moves into alignment with source 38 and sensor 40, and the sensor develops a fifth sync pulse which is the reference (REF) sync pulse. At this time, the reference filter 28d moves into alignment with sample cell window 20. The IR detector receives IR from the sample cell in the transmission bandwidth of the reference filter, and the detector develops a reference (REF) video pulse proportional to the received radiation. Thereafter, enlarged slot 56, formed at the filter wheel periphery, moves into alignment with source 38 and sensor 40, and the sensor develops a sixth pulse which is the RESET sync pulse. At this time, no filter is in alignment with sample cell window 20 and no video pulse is developed by the IR sensor. As described more fully hereinafter, all gas channels are reset upon detection of the RESET sync pulse in preparation for the next cycle or sequence of sync and video pulses.

The preferred geometry of the interior wall of sample cell 16 is conical so that IR reflected from the cell wall does not reach the IR detector 32. This eliminates the hydrocarbon "hang-up" problem which is characteristic of conventional sample cells. Thus, in conventional gas analyzers the sample cell interior wall is cylindrical. As a result, IR radiation reflecting off HC which has been absorbed in the cell wall from a prior gas mixture will reach the detector and produce a spurious HC signal. In the present invention, the cell wall is tapered and the IR detector is spaced from the cell such that reflected IR cannot reach the detector.

In addition, since the gas inlet and outlet ports are spaced laterally along the cell axis in the present invention, dead zones in the flow of sample gas through the cell are eliminated, thereby minimizing the response time of the unit.

The IR detector 32 and filter wheel 26 are mounted in a black Valox receiver enclosure 58. See FIG. 6. The IR detector is temperature stabilized in order to achieve a reasonably flat response between 3-5 microns. Preferably, the detector is a lead selenide detector with an operating temperature of 4° C. The detector is mounted on a single-stage thermo-electric cooler 60. A miniature bead thermistor 62 is also mounted on cooler 60. The cooler 60 and thermistor 62 are part of the IR detector temperature control 34 (FIG. 2). Detector temperature is lowered by passing electrical current through the cooler 60. If the detector temperature begins to rise, the resistance of the thermistor 62 decreases and the temperature control 34 responds by increasing the cooler current, thereby returning the detector temperature to 4° C. Conversely, if the detector temperature begins to drop, the thermistor resistance increases and the controller responds by decreasing the cooler current, thereby returning the temperature to 4° C.

Figure 6:
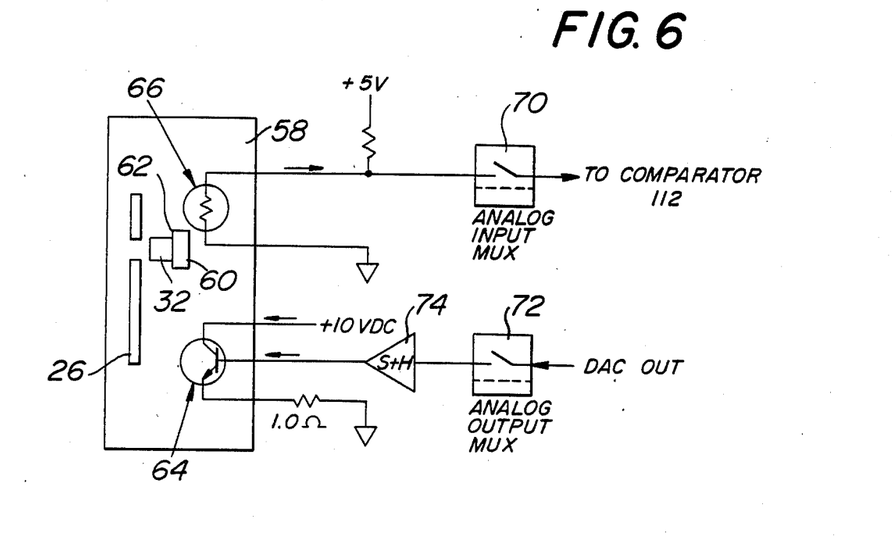
FIG. 6 is a schematic of the filter wheel temperature stabilization portion of the gas analyzer.

The filter wheel 26 is also temperature stabilized. A heater 64, which is a NPN power transistor, is mounted within enclosure 58 near the filter wheel. A thermistor 66 is also mounted in the enclosure near the filter wheel. The thermistor 66 is connected to digital processor 140 via analog input multiplexor 70. The heater transistor 64 is driven by the output of DAC 114 analog output demultiplexor 72 and a sample and hold gate 74 in network 119. (FIG. 1B).

The temperature of the filter wheel, i.e., the temperature within receiver enclosure 58, is controlled in three stages by the digital processor. In the first or "preheat" stage immediately following application of power to the unit, the digital processor causes DAC 114 to generate a high analog power level signal to the heater 64 via analog output demultiplexor 72 and sample and hold gate 74. The output of the sample and hold gate drives heater transistor 64 so as to rapidly preheat the interior of the receiver enclosure. The digital processor samples the thermistor 66 output via analog input multiplexor 70 and comparator 112. The processor compares the thermistor output with a preselected threshold temperature which is a constant stored in memory. When the preselected temperature is reached, the digital processor transfers to the second or "initialize" stage, causing the DAC 114 to drive transistor 64 via demultiplexor 72 and sample and hold gate 74 at a lower analog power level. Accordingly, the transistor continues to drive the receiver enclosure to the desired temperature. In this manner, the interior of the receiver enclosure is rapidly brought to a point near the desired temperature without "servoing" the output of sample and hold gate 74.

In the "initialize" stage, the digital processor compares the thermistor output to another threshold which is a constant stored in memory. When the threshold is reached, the processor transfers to the third or "tracking" stage. In the "tracking" stage, the thermistor 66 is continuously monitored to determine the temperature error, i.e., the difference between the desired temperature, which is a constant stored in memory, and the actual enclosure temperature which is indicated by the thermistor. The drive to heater transistor 74 is continuously adjusted in the "tracking" stage so as to null the temperature error and maintain the interior of the receiver enclosure at the desired temperature.

Figure 7:
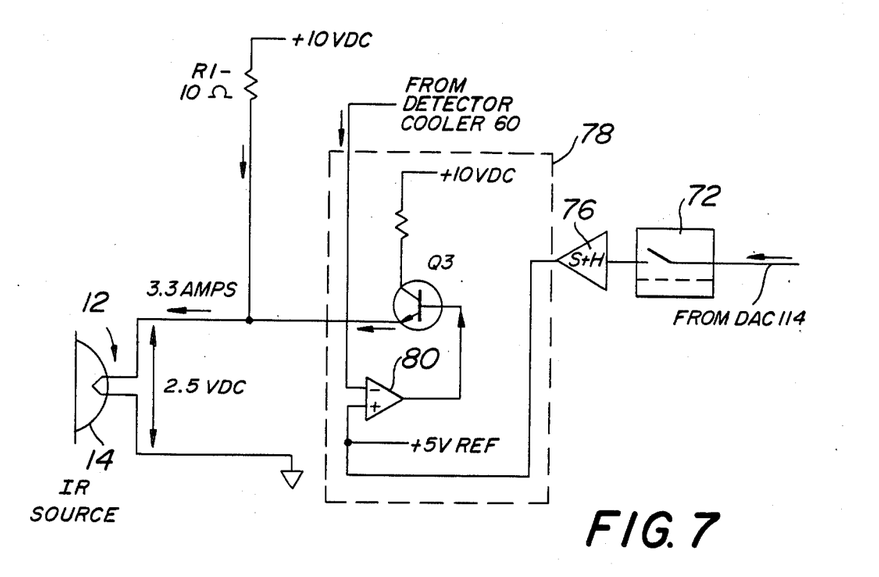
FIG. 7 is a block diagram of the IR source drive control portion of the gas analyzer.

The IR source 12 is also controlled by the digital processor 140. Control is exercised via analog output demultiplexor 72, a sample and hold gate 76 in network 119, and a source driver 78. See FIG. 7. The source driver 78 is shown schematically in FIG. 7 as a driver transistor Q3 and amplifier 80. The DAC 114 and sample and hold gate 76 drive amplifier 80 so as to cause transistor Q3 to supply current to IR source 12. The amplifer is driven such that the sum of the currents supplied by the transistor, the cooler 60 and a resistor R1 is maintained constant, preferably at 3.3 amperes. Approximately 0.75 amperes is supplied through resistor R1 and an additional 0–2.0 amperes is provided by cooler 60. The remaining current requirement of 0.55–2.55 amperes is supplied via a transistor Q3 under control of the digital processor and DAC.

For each rotation of filter wheel 26, six sync pulses are generated by sensor 40, viz, the BKGD, HC, CO, CO2 and REF sync pulses and the RESET sync pulse. See FIG. 5. Timing for the digital processor is developed by the sync network 82. See FIG. 8. The sync network includes a reset detector 84 which detects the RESET sync pulse and which resets a sync counter 86 in response. The RESET sync pulse is also transmitted to the interrupt input of the digital processor.

Figure 8:
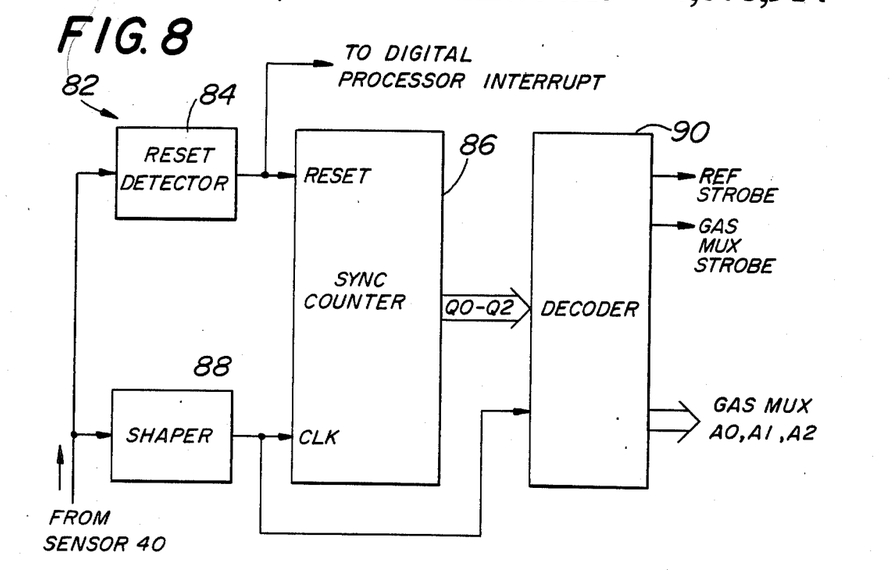
FIG. 8 is a block diagram of the synchronization network.

The sync counter is a three-stage counter which is incremented by the output pulses generated by a shaper circuit 88. Each pulse output of the shaper circuit corresponds to a sync pulse at the sensor 40 output. The state of the sync counter, i.e., the outputs of the counter stages, are decoded by a decoder 90 into the decoder outputs GAS MUX A0–A2. After being shaped, the sync pulses generated by sensor 40 appear serially at the GAS MUX STROBE output of the decoder. When the outputs of sync counter 86 indicate that the counter has reached the count of five, corresponding to the REF sync pulse, a pulse is generated at the REF STROBE output of the decoder.

The GAS MUX A0, A1 and A2 outputs of the decoder indentify the first through fourth sync pulses i.e., BKGD, HC, CO and CO2 sync pulses. The GA MUX A0, A1 and A2 outputs form a three-bit address which is used to gate samples of the video preamplifier 54 output to the digital processor as described hereafter.

Figure 9:
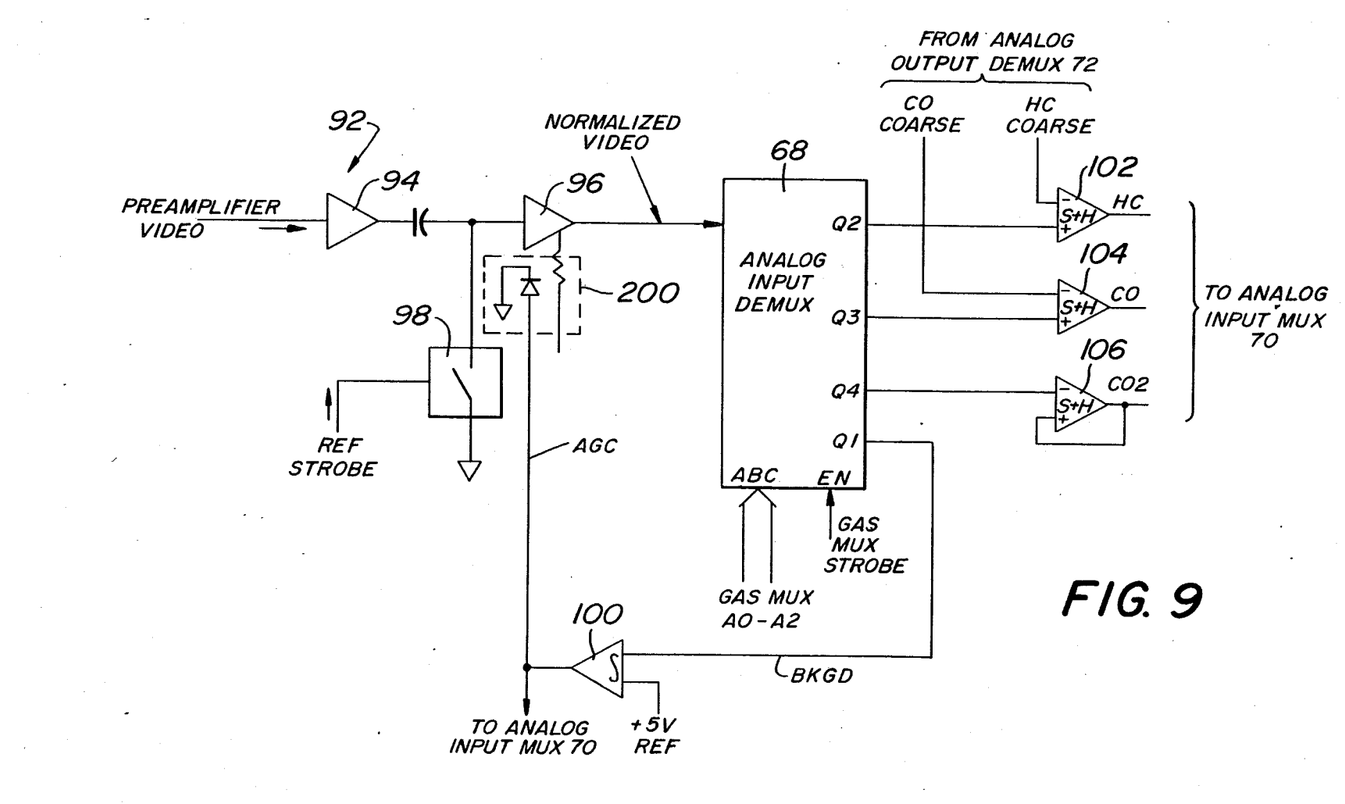
FIG. 9 is a block diagram of the video preprocessor.

The video preprocessor is shown in greater detail in FIG. 9. Preprocessor 92 includes a fixed gain amplifier 94 and a variable gain amplifier 96. Amplifier 96 is provided with a variable resistance 200 which is varied by an optically coupled AGC signal. Operation of resistance 200 is described more fully hereinafter.

When the first pulse in a cycle is generated, i.e., the BKGD sync pulse, the BKGD video pulse is transmitted to analog input demultiplexor 68. See FIG. 9. The demultiplexor transmits the BKGD video pulse to an AGC amplifier 100. The AGC amplifier 100 generates an AGC signal which is proportional to the amplitude of the BKGD video pulse. The AGC signal is optically coupled to resistance 200 so as to alter the gain of amplifier 96 and maintain the video output between samples at a fixed 5 volt reference level. In addition, the BKGD video sample is fed to the digital processor which stores the sample and uses the sample to offset the HC and CO channel signals so as to compensate for any error produced by background IR. It is not necessary to compensate the CO2 video sample for background IR since the CO sample is much larger than the BKGD sample.

Figure 10:
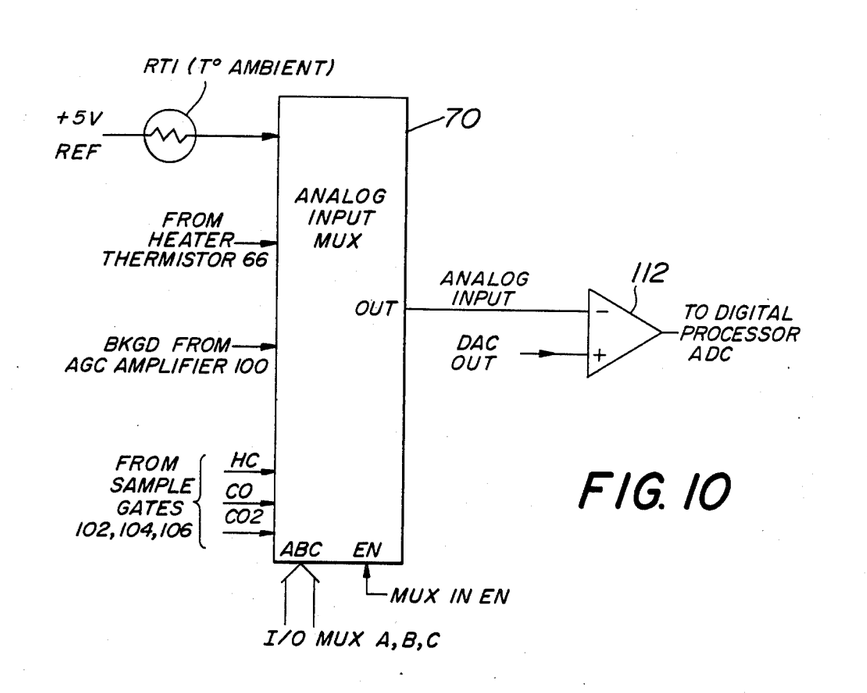
FIG. 10 is a schematic of the analog input multiplexor and comparator portion of the analog to digital conversion (ADC)channel.

When a HC video pulse occurs, it is transmitted by demultiplexor 68 to sample and hold gate 102. See FIG. 9. The output of the sample and hold gate is transmitted to analog input multiplexor 70. See FIG. 10. When a CO video pulse is generated, the demultiplexor 68 transmits the pulse to sample and hold gate 104. See FIG. 9. The output of the sample and hold gate is also transmitted to the analog input multiplexor 70. See FIG. 10. When a CO2 video pulse is generated, demultiplexor 68 transmits the pulse to sample and hold gate 106. See FIG. 9. The output of the sample and hold gate is also transmitted to the analog input multiplexor 70. See FIG. 10.

When a REF video pulse is generated the REF STROBE pulse closes an analog switch 98 in the preprocessor. See FIG. 9. The switch clamps the REF video output of amplifier 94 to ground. When the REF STROBE pulse ends, analog switch 98 is opened, thereby removing the ground clamp. The ground clamped REF video pulse is amplified by variable gain amplifier 96 to provide a 5 volt AGC ground clamped signal at the amplifier output.

Figure 11:
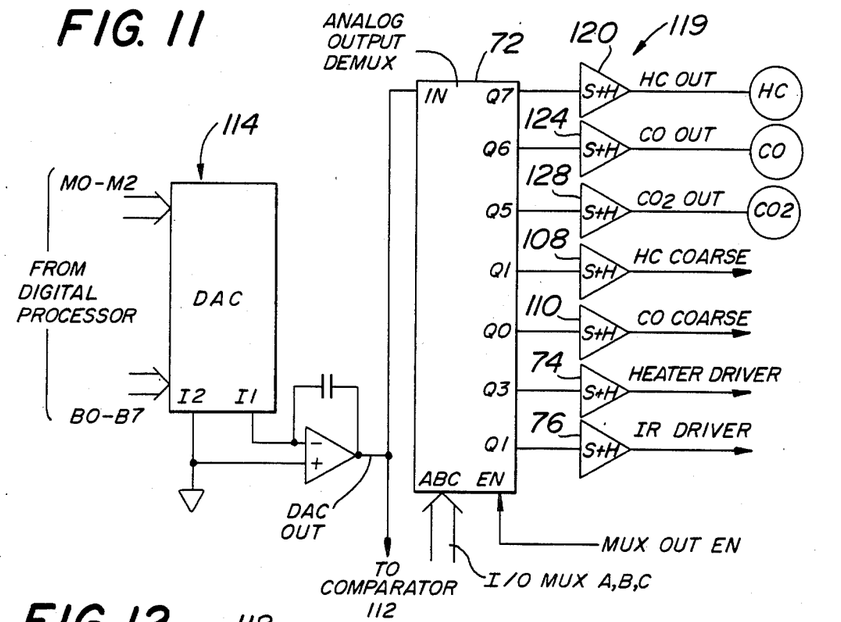
FIG. 11 is a schematic of the digital to analog converter (DAC), analog output demultiplexor and sample and hold network.

When the HC and CO video pulses are generated, the sample and hold gates 102, 104 offset the HC and CO video pulses by HC and CO coarse signals. See FIG. 9. The HC and CO coarse signals are computed by the digital processor based on the valve of the BKGD video sample. The HC and CO coarse signals are generated by the digital processor and are transmitted by the analog output demultiplexor 72 to the sample and hold gates 102, 104. See FIG. 11.

The output of analog input multiplexor 70 contains the coarse corrected analog HC and CO samples and the analog CO2 sample. The output is transmitted to voltage comparator 112 for digitizing. See FIG. 10. The other input to the comparator is the output of DAC 114. Each coarse corrected HC and CO sample, and each CO2 sample, which appears at the input of comparator 112 is digitized by matching the sample with the DAC 114 output. During digitization, successive multiple bit sample approximations (MO-M2 and BO-B8) are generated by the digital processor and converted to analog by the DAC. See FIG. 11. The coarse corrected sample at the input of comparator 112 is compared with each analog approximation at the DAC output until a match is achieved. See FIG. 10. Thus, each gas channel sample is digitzed using a successive-approximation technique.

Figure 12:
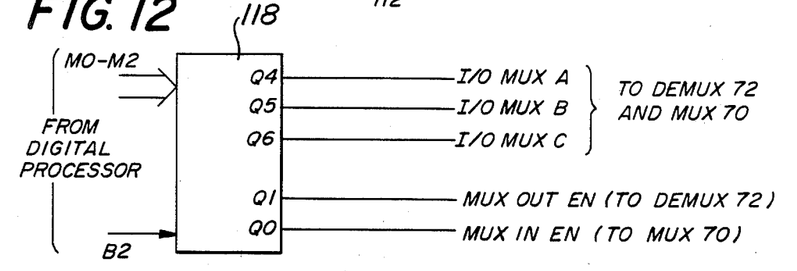
FIG. 12 is a schematic of the addressable latch which controls the input and output multiplexing and demultiplexing.

After digitization of a gas channel sample, the digital processor processes the sample and transmits a multiple bit signal (MO-M2 and B2) to an addressable latch 118. See FIG. 12. The outputs of the addressable latch include the I/O MUX A, B and C signals and the MUX OUT EN signal. The I/O MUX A, B and C signals indentify the output lines of analog output demultiplexor 72. See FIG. 11. The MUX OUT EN signal enables the analog output demultiplexor 72 to transmit the process gas channel sample at the DAC output to appropriate sample and hold gates in network 119 as indicated by the I/O MUX A, B, and C signals. Thus, during a HC video pulse, the DAC output is transmitted to sample and hold gate 120, and the sample and hold gate drives the HC meter. See FIG. 11. During the CO video pulse, the DAC output is transmitted to sample and hold gate 124, and the sample and hold gate drives the CO meter. During the CO2 video pulse, the DAC output is transmitted to sample and hold gate 128, and the sample and hold gate drives the CO2 meter.

Figure 13:
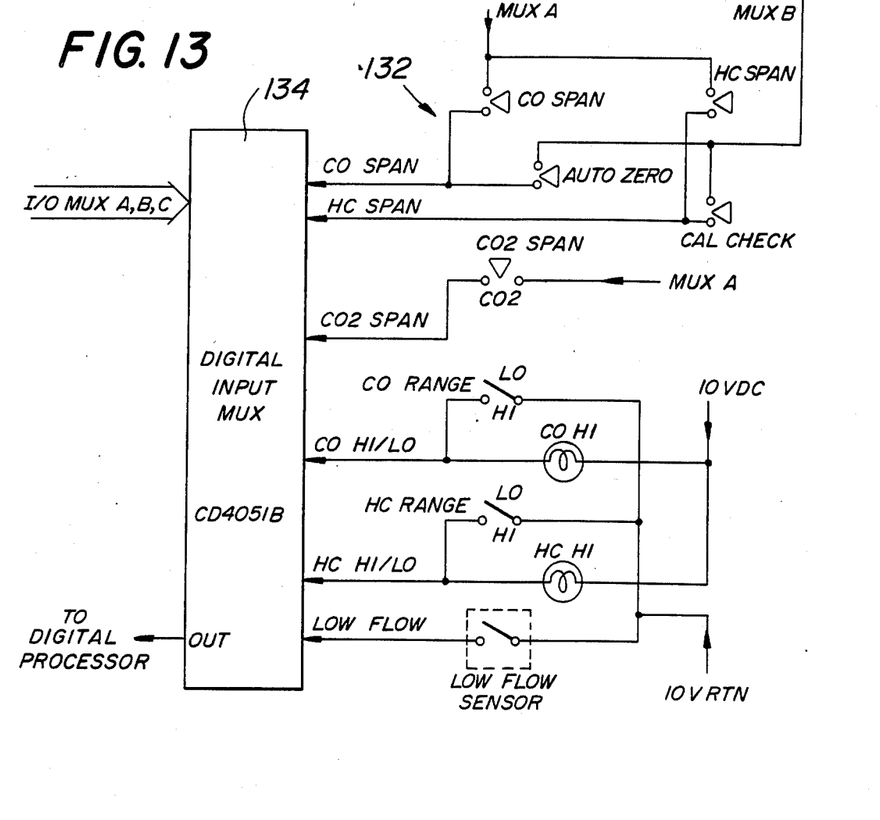
FIG. 13 is a schematic of the panel switches and digital input multiplexor.
Figure 14:
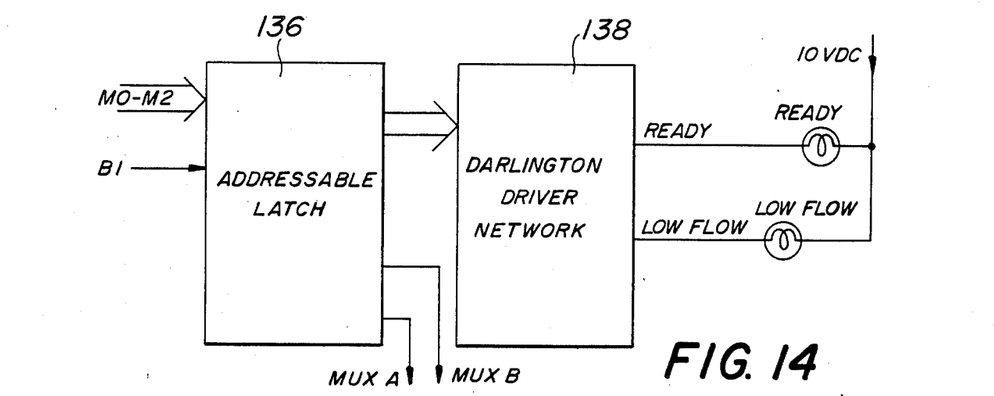
FIG. 14 is a schematic of the addressable latch and driver which control the panel switches and READY and LOW FLOW lamps.

The panel switches, designated generally as 132 in FIG. 13, comprise a CO SPAN switch, and HC SPAN switch, a CO2 SPAN switch, a CAL CHECK switch, an AUTO ZERO switch, a CO RANGE switch and a HC RANGE switch. The CO SPAN, CO2 SPAN and HC SPAN switches are periodically polled by a MUX A signal. The AUTO ZERO and CAL CHECK switches are periodically polled by a MUX B signal. Closure of any of these switches couples the MUX A or MUX B signal to the digital processor via the digital input multiplexor 134. See FIG. 13. The MUX A and MUX B signals are complementary logic signals which are generated by an addressable latch 136 in response to the MO-M2 and B1 outputs of the digital processor. See FIG. 14.

The addressable latch 136 also drives a Darlington drive network 138. The Darlington drive netowrk generates READY and LOW FLOW signal outputs which operate READY and LOW FLOW lamps. The READY lamp is actuated when the desired temperature for enclosure 58 has been reached. This is detected by the digital processor as previously described. The LOW FLOW lamp is actuated when a LOW FLOW sensor (FIG. 13) closes (from the normally open position) upon detecting a drop in gas flow to the sample cell. The LOW FLOW sensor is coupled to a flow conduit which conducts sample gas to the sample cell. Upon closure of the LOW FLOW sensor, the LOW FLOW input signal to digital input multiplexor 134 is transmitted at the multiplexor output to the digital processor. In response, the digital processor operates latch 136 (Figure 14) so as to cause Darlington driver network 138 to generate the LOW FLOW signal.

As previously indicated, the analyzer of the present invention includes a HC meter, CO meter and CO2 meter. See FIG. 11. The HC meter measure N-hexane concentration in parts per million by volume and is provided with high and low range scales. The high range scale is 0-2000 ppm, and the low range scale is 0-400 ppm. The CO meter measures CO concentration in percent by volume and is also provided with high and low range CO scales. The high range CO scale is 0-10%, and the low range CO scale is 0-1.0%. The CO2 meter is utilized to measure CO2 concentration in percent by volume. The CO2 scale is a single range scale extending from 0-16%.

The CO and HC RANGE switches select the high or low range scales for the CO and HC meters. The selection is indicated on the output line of multiplexor 134. The digital processor selects appropriate linearization functions for the CO and HC channels based on the selection.

To zero the meters, the sample cell is evacuated. If the HC, CO or CO2 meter needle is not at zero, the operator depresses the AUTO ZERO switch. See FIG. 13. The digital processor automatically adjusts the HC, CO and CO2 channel gains so that the analog output demultiplexor 72 generates HC OUT, CO OUT, and CO2 OUT signals which zero the meter needles.

To calibrate the meters, when the sample cell is evacuated or when gas sample flows through the cell, the operator first depresses and releases the AUTO ZERO switch and then depresses and holds the CAL CHECK switch. If the HC meter does not indicate at the CAL line on the meter scale, which is preferably 80% of the full scale reading, the operator depresses and holds the HC SPAN switch. The digital processor operates the analog output multiplexor 72 so as to generate an increasing or decreasing HC OUT signal. When the HC meter reaches the CAL line, the operator releases the CAL CHECK and HC SPAN switches. The CO and CO2 meter scales are provided with CAL lines and are calibrated in the same manner by operation of the CO and CO2 SPAN switches.

The digital processor gas channel gains are calibrated by introducing known concentrations of constituent gases in the sample cell. For example, a predetermined concentration of HC, CO or CO2 is introduced into the sample cell, and the AUTO ZERO switch is depressed and then released. The operator then depresses and holds the HC, CO or CO2 SPAN switch. In response the digital processor increases or decreases the HC OUT, CO OUT or CO2 OUT signal. When the signal causes the associated meter to indicate the known concentration or amount on the meter scale, the SPAN switch is released.

The digital processor 140 is preferably a CDP 1802C microprocessor driven off a 3.5795 Mhz crystal clock. The processor is provided with RAM and ROM for temporary and permanent storage. The processor program is stored in ROM. General operation of the digital processor is exemplified in FIGS. 15A–G and FIG. 16.

Upon application of power, the processor executes and Initilize routine wherein all variables are initialized and RAM is cleared. The operation of the digital processor is organized into non-overlapping time frames A, B and C. See FIGS. 15 and 16. Frames A, B and C are time periods during which the digital processor executes specific functions as described hereafter. Each frame is 66.7 milliseconds long. Frame A occurs at 133 millisecond intervals. Frame B occurs at 267 millisecond intervals as does frame C. Each frame is defined by five consecutive RESET sync pulses, corresponding to four revolutions of the filter wheel. During the first four RESET sync pulses, i.e., the first three revolutions of the filter wheel, the HC, CO and CO2 gas channel samples are processed. During the fourth revolution of the filter wheel, the digital processor performs housekeeping functions. See FIG. 16.

Each RESET sync pulse is transmitted to the Interrupt input of the digital processor as previously explained. In each of frames A, B and C, the digital processor saves all internal register contents upon receiving an interrupt signal. See FIG. 15B. The digital processor counts the number of interrupt signals received during any frame and determines whether a HC, CO or CO2 gas channel should be processed or whether housekeeping functions should be performed based on the number of interrupt signals received. At the reception of the first interrupt signal, the digital processor processes the signal in the HC gas channel. See FIG. 16. Upon receipt of the second interrupt signal, the digital processor processes the signal in the CO gas channel. Upon receipt of the third interrupt signal, the digital processor processes the signal in the CO2 gas channel. When the fourth interrupt signal is received, the digital processor performs no signal processing but, instead, performs various housekeeping functions and then restores all registers and returns to the main program.

Figure 15A:
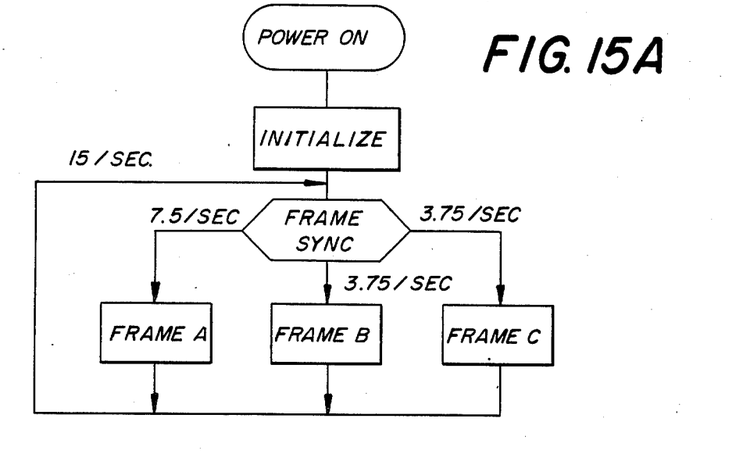
FIGS. 15A-G comprise a flow chart of the analyzer software.
Figure 15B:
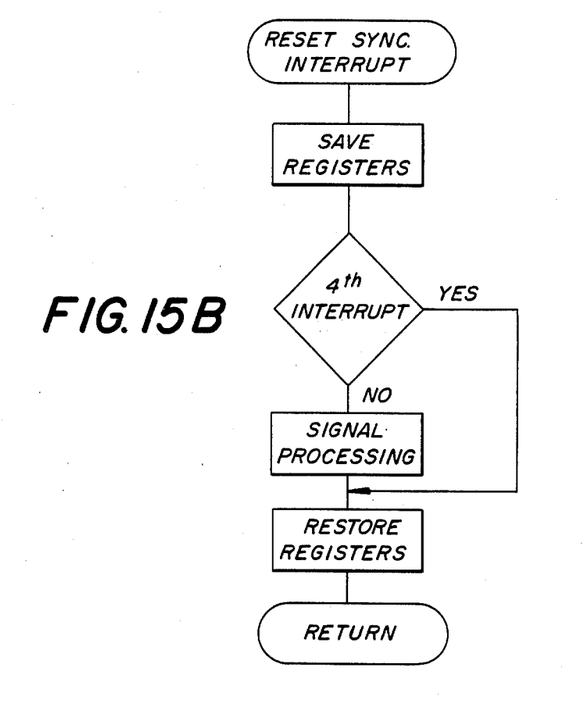
Figure 15C:
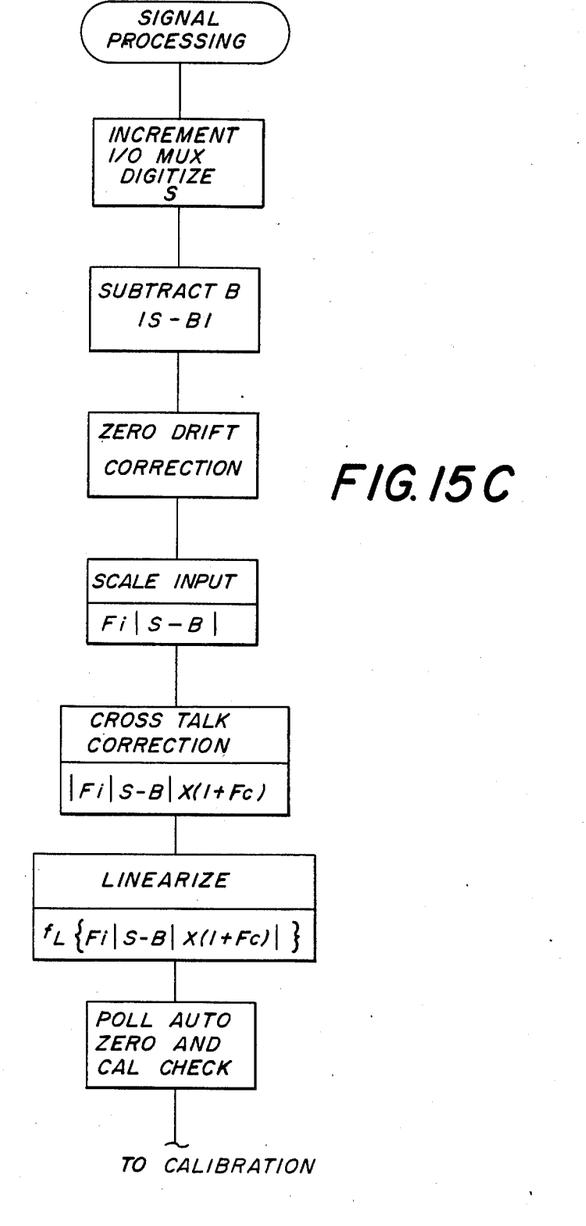
Figure 15D:
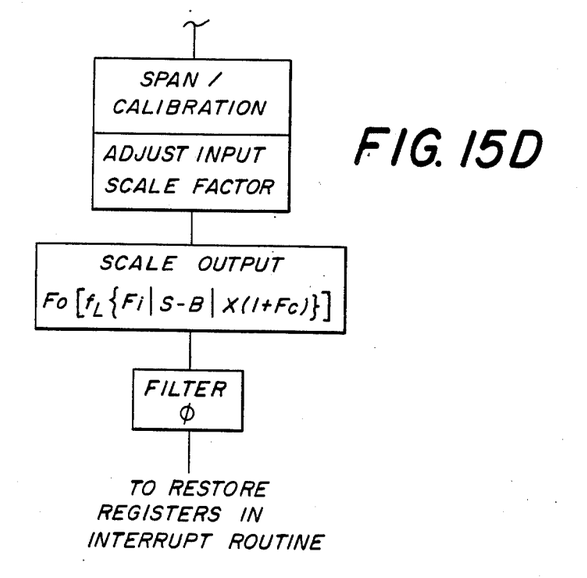
Figure 15E:
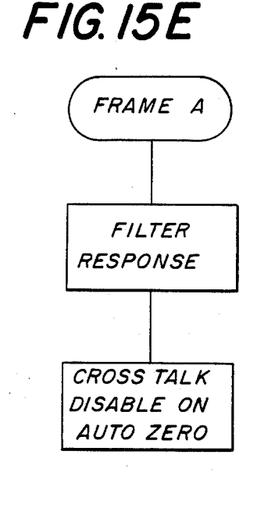
Figure 15F:
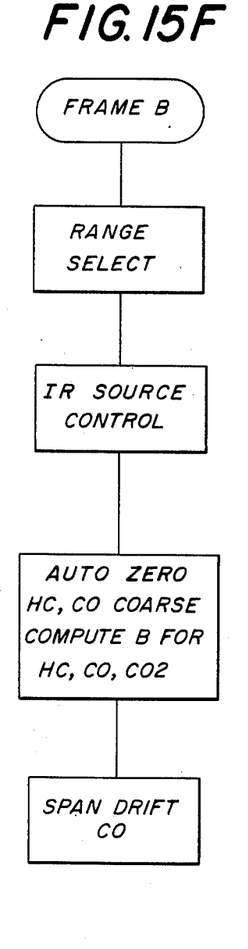

The signal processing routines are shown in FIGS. 15C and D. The HC, CO and CO2 gas channel samples are processed separately and consecutively in each frame. Initially, the digital processor increments the I/O MUX A, B, C outputs and interacts with the DAC 114 and comparator 112 to digitize the gas channel sample as already explained. The digitized sample S is then offset by a variable B which is a bias computed by the digital processor during ane AUTO ZERO operation. The absolute value of the difference between the digitized sample S and the bias B is then taken and corrected for zero drift based on the output of thermistor RT1 (FIG. 1A). The sample is then multipled by an input scale factor Fi which is retrieved from memory. The scale factor is computed and stored in memory when the unit is calibrated with respect to a known constituent gas concentration as already described.

The scaled sample is then corrected for cross-talk between channels by multiplying the scaled sample by the factor $(1+Fc)$. The factor is a constant which is stored in memory and retrieved when needed. Thereafter, the scaled, corrected sample is linearized. The linearization function fL is stored in memory. Different linearization functions are used for different ranges of each meter scale. Selection of a particular linearization function is based on the position of the HC and CO RANGE switches which are inspected during frame B as described hereafter.

Following linearization, the AUTO ZERO and CAL CHECK switches are polled. The digital processor will adjust he input scale factor thereafter based on the operation of the SPAN switches as already described. The digital processor then applie an output scale factor F0 and digitally filters the channel sample. The filtered signal is converted to analog by the DAC to drive the analog meters.

General operation of the digital processor in frames A, B and C is shown in FIGS. 15B–G. In frame A, the digital processor determines the response time for the digital filter for each gas channel. If the AUTO ZERO switch is depressed, the processor disables the cross-talk correction so that an accurate determination can be made of the bias B.

During frame B, the processor selects the appropriate linearization function based on the state of the HC and CO RANGE switches. See FIG. 15F. The processor then adjusts the drive to the IR source as previously described. Thereafter, the processor determines the HC and CO coarse signal levels and computes the bias B for the HC, CO and CO2 channels during an AUTO ZERO operation. The CO gas channel is then corrected for span drift based on the output of ambient thermistor RT1 (FIG. 1A).

Figure 15G:
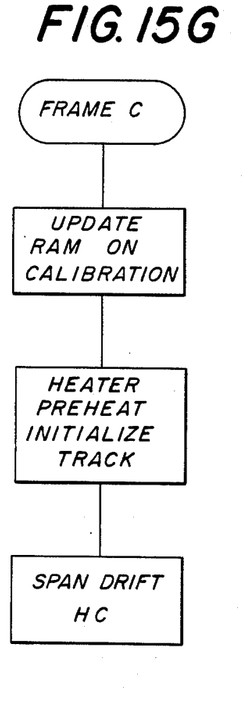
Figure 16:
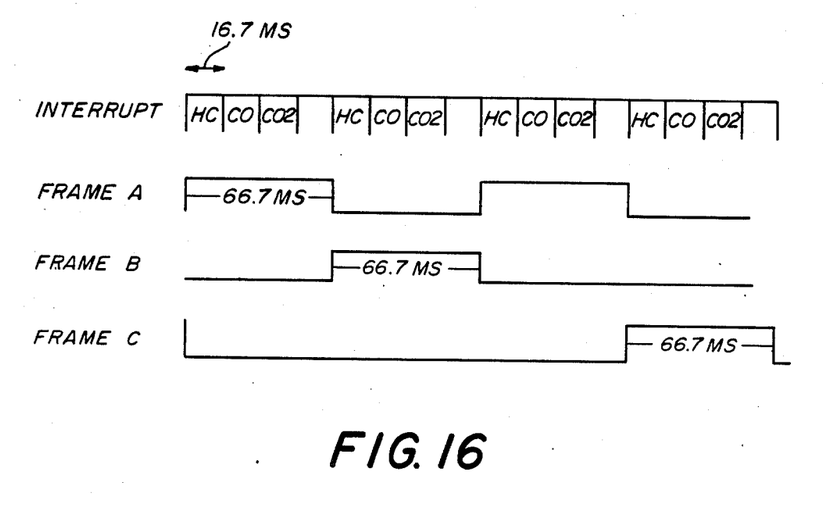
FIG. 16 shows the software timing.

In frame C, the digital processor updates all RAM variables at the end of a calibration operation. The digital processor then controls the filter wheel heater as previously explained. Thereafter, the processor corrects the HC channel for span drife based on the output of thermistor RT1 (FIG. 1A).

The present invention many be embodied in other specific forms without departing from the spirit or essential attributes thereof and, accordingly, reference should be made to the appended claims, rather than to the foregoing specification, as indicating the scope of the invention.

We claim:

1. Digital IR gas analyzer, comprising:
a sample cell having an inlet port and an outlet port for conducting a gas sample therethrough,
an IR radiation source,
means for producing a series of IR radiation samples of the constituents of said gas sample,
means for generating a fixed-amplitude non-background-compensated reference pulse,
means for producing a series of non-background-compensated normalized video pulses corresponding to said constituent radiation samples, said video pulse being normalized with respect to a precision reference voltage and the amplitude of said reference IR pulse,
means for converting said normalized video pulse into digital signals,
means for digitally processing said digital signals, including means for compensating said digital signals for background IR radiation,
means for converting the processed digital signals to analog signals, and means for driving one or more analog meters in response to the analog signals.

2. Digital IR gas analyzer according to claim 1, wherein said means for producing IR radiation samples include a filter wheel, means for rotating said filter wheel at a constant speed, an interference filter for each gas constituent disposed along a radius of the filter wheel, a reference interference filter disposed along a radius of the filter wheel, means disposed on a radius of the filter wheel for blocking the transmission of IR radiation from said IR radiation source to said means for producing a series of normalized video pulses, and means for maintaining the filter wheel at a constant temperature.

3. Digital IR gas analyzer comprising:
a sample cell having an inlet port and an outlet port for conducting a gas sample therethrough,
an IR radiation source,
an IR radiation detector,
means for maintaining said IR detector at a constant temperature,
means for producing a series of IR radiation samples of the constituents of said gas sample comprising a filter wheel disposed between said sample cell and said IR detector, means for rotating said filter wheel at a constant speed, an interference filter for each gas constituent disposed on a radius of the filter wheel, a reference interference filter disposed on a radius of the filter wheel, means disposed on a radius of the filter wheel for blocking the transmission of IR radiation from said source to said detector, and means for stabilizing the temperature of the filter wheel,
means for generating a fixed-amplitude, non-background-compensated reference pulse,
means for producing a series of normalized video pulses corresponding to said constituent radiation samples, said video pulses being normalized with respect to a precision reference voltage and to the amplitude of said reference pulse,
means for converting said normalized video pulses into digital signals,
means for digitally processing said digital signals, including means for compensating said digital signals for background IR radiation,
means for converting the processed digital signals to analog signals, and
means for driving one or more analog meters in response to the analog signals.

4. Digital IR gas analyzer according to claim 3, wherein the means for maintaining said IR detector at a constant temperature comprises thermoelectric cooling means in thermal contact with said IR detector.

5. Digital IR gas analyzer according to claim 3, wherein the means for stabilizing the temperature of the filter wheel comprises:
an enclosure encompassing said filter wheel and said IR detector,
heating means in said enclosure,
circuit means for causing the heater to operate at a first power level for rapidly preheating the interior of the enclosure to a first preselected temperature,
circuit means for causing the heater to operate at a second lower power level after said first preselected temperature is reached so as to heat the interior of the enclosure to a second preselected temperature, and
circuit means for controlling the heater to maintain said second preselected temperature within preselected limits after said second preselected temperature is reached.

6. Digital gas analyzer according to claim 1 or 3, further comprising:
means for automatically zeroing said meters simultaneously in the absence of a gas sample from said sample cell, and
means for automatically calibrating each of said one or more meters for known concentrations of constituents of said gas sample in said sample cell.

* * * * *